United States Patent
Garman

(10) Patent No.: US 6,712,611 B2
(45) Date of Patent: Mar. 30, 2004

(54) ENDODONTIC INSTRUMENT WITH CONTROLLED FLEXIBILITY AND METHOD OF MANUFACTURING SAME

(75) Inventor: Gary T. Garman, La Verne, CA (US)

(73) Assignee: Ormco Corporation, Orange, CA (US)

( * ) Notice: Subject to any disclaimer, the term of this patent is extended or adjusted under 35 U.S.C. 154(b) by 188 days.

(21) Appl. No.: 09/972,104

(22) Filed: Oct. 5, 2001

(65) Prior Publication Data

US 2003/0068597 A1 Apr. 10, 2003

(51) Int. Cl.⁷ ................................................ A61C 5/02
(52) U.S. Cl. ...................................................... 433/102
(58) Field of Search ........................... 433/81, 102, 224

(56) References Cited

U.S. PATENT DOCUMENTS

| | | | |
|---|---|---|---|
| 1,067,015 A | * 7/1913 | Fowler | |
| 4,260,379 A | 4/1981 | Groves et al. | 433/102 |
| 5,106,298 A | 4/1992 | Heath et al. | 433/102 |
| 5,380,200 A | 1/1995 | Heath et al. | 433/102 |
| 5,464,362 A | 11/1995 | Heath et al. | 451/48 |
| 5,628,674 A | 5/1997 | Heath et al. | 451/48 |
| 5,876,202 A | * 3/1999 | Berlin | 433/102 |
| 5,882,198 A | * 3/1999 | Taylor et al. | 433/102 |
| 5,984,679 A | 11/1999 | Farzin-Nia et al. | 433/102 |
| 6,299,445 B1 | * 10/2001 | Garman | 433/102 |
| 6,315,558 B1 | * 11/2001 | Farzin-Nia et al. | 433/102 |
| 6,382,973 B2 | * 5/2002 | Murai et al. | 433/102 |
| 6,409,506 B1 | * 6/2002 | Graybill | 433/102 |

OTHER PUBLICATIONS

Kerr Corporation, *New Kerr K–Flex Instrument*, Brochure, 7 pgs., Feb. 1981.

Dr. Edgar Schäfer, *Relationship Between Design Features of Endodontic Instruments and Their Properties, Part 1: Cutting Efficiency*, Article, 4 pgs., undated.

Dr. Edgar Schäfer, *Relationship Between Design Features of Endodontic Instruments and Their Properties, Part 2: Instrumentation of Curved Canals*, Article, 4 pgs., undated.

* cited by examiner

Primary Examiner—Ralph A. Lewis
(74) Attorney, Agent, or Firm—Wood, Herron & Evans, L.L.P.

(57) ABSTRACT

An endodontic instrument and method of manufacturing an instrument including an elongate member having a longitudinal axis, a proximal end, a distal end and a working length between the proximal and distal ends. The working length is formed with a plurality of surface portions ground from the outer surface thereof along paths extending along the longitudinal axis. One or more edges formed during the initial grinding operations are then at least partially ground down. The ground blank is then physically twisted to form helical cutting and/or debris removal edges extending around the longitudinal axis. The instrument may be a file or reamer used in root canal procedures and may have three, four or more longitudinally extending surface portions and multiple edges. Flexibility of the instrument may also be easily varied according to the invention.

18 Claims, 6 Drawing Sheets

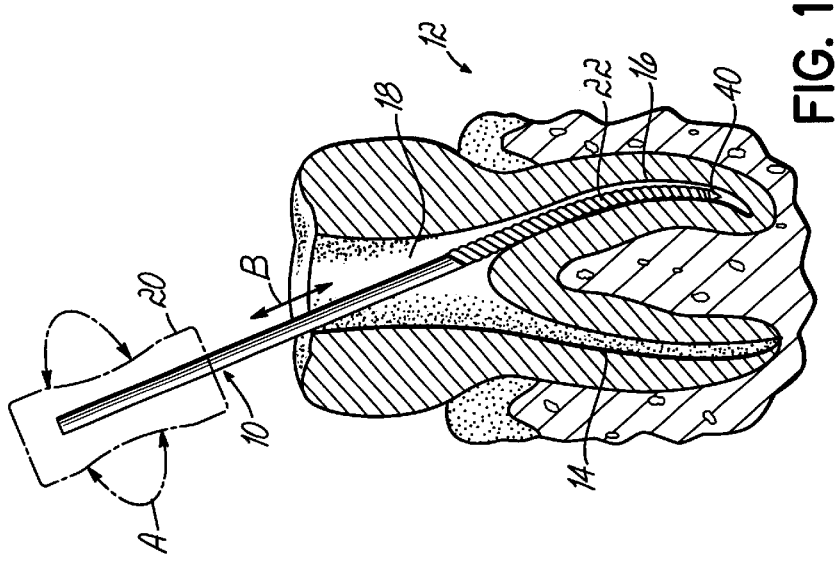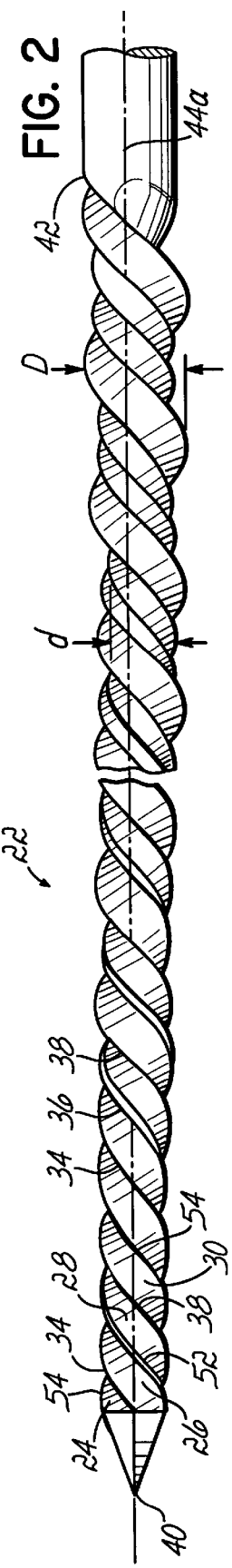

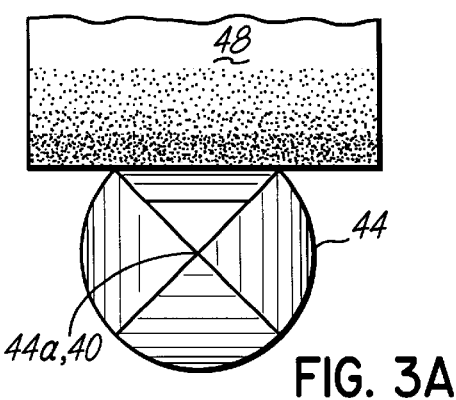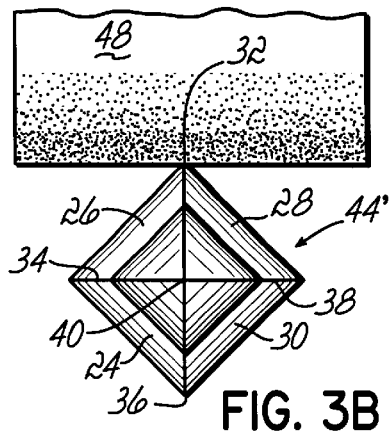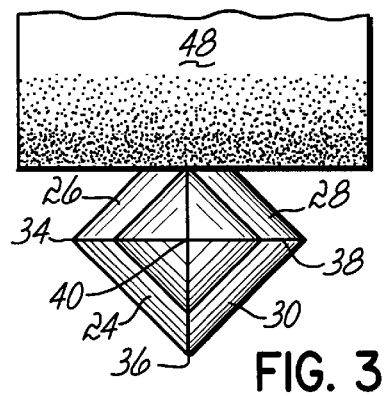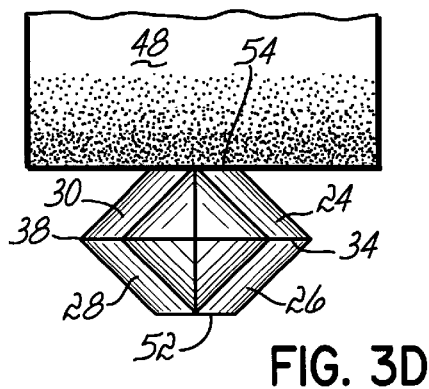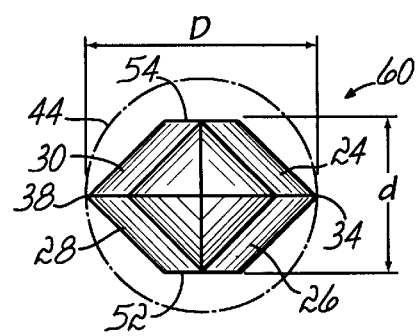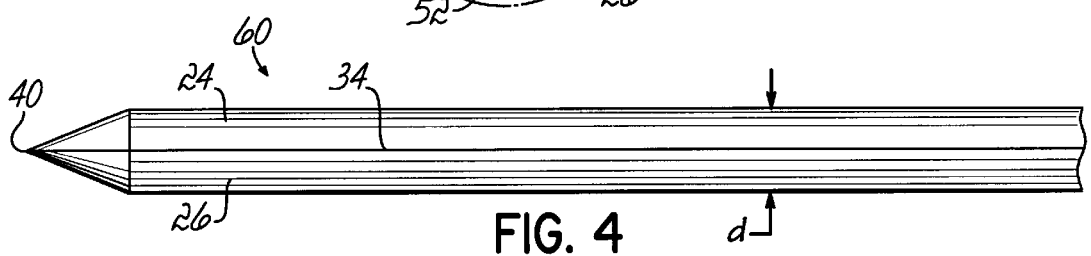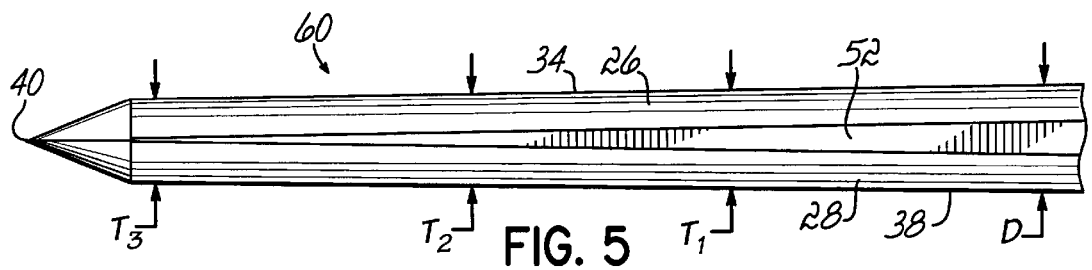

ENDODONTIC INSTRUMENT WITH CONTROLLED FLEXIBILITY AND METHOD OF MANUFACTURING SAME

FIELD OF THE INVENTION

The present invention relates generally to endodontic instruments, such as files and reamers and, more specifically, to those instruments especially useful in root canal procedures.

BACKGROUND OF THE INVENTION

Endodontists use various types of instruments for cleaning and enlarging the root canals of the teeth. In a typical root canal procedure, an endodontist first makes an opening in the surface of the tooth to provide access to the interior. The endodontist then utilizes small instruments, such as hand held files and reamers, to clean and enlarge the narrow, tapered root canals. In a conventional procedure, the endodontist fills the prepared root canals with gutta percha, which is a rubber-like substance, and then seals the tooth with protective cement. The endodontists may sometimes apply a crown to the tooth as a final step.

Typically, the endodontist uses a series of delicate, flexible files to clean out and shape the root canals. Each file includes a proximal end which includes a handle to be gripped between the fingers of the endodontist. The files each further include a distal end or tip. A working length with helical flutes and cutting edges is located between the proximal and distal ends. The endodontist uses files of increasingly larger diameter to sequentially increase the diameter of the root canal and achieve the desired diameter and shape.

Endodontic root canal files and reamers have been formed from twisted blanks in generally three different configurations. One type is formed by twisting a ground blank having a square cross section to create four helical cutting edges per revolution. Another type consists of a twisted blank of triangular cross section having three cutting edges per revolution. The third type, often referred to as a K-flex type, is formed from a blank having a parallelogram-shaped cross section, such as a rhomboid-shaped cross section. After twisting this type of blank, two cutting edges and two debris removal edges will be formed per revolution. All three of these types of instruments have a tapered major diameter or cross-sectional dimension and a tapered minor diameter or cross-sectional dimension in which the taper angles are generally the same. Also, the angles formed between the surfaces that define the cutting and debris removal edges are constant along the length of the instrument. In other words, a given grind angle of an edge on the instrument remains the same along the entire working length of that instrument.

Existing endodontic files and reamers formed from twisted blanks are designed in such a manner that the minor diameter is purely a function of the major diameter. The undesirable consequences of this type of design become significant for instruments that have a greater taper along the working length. In particular, these instruments become much stiffer toward the proximal end or handle of the instrument. This can cause the instrument to be difficult to maneuver within curved root canals because the instrument may not flex enough to conform to the shape of the canal. Although certain helically fluted endodontic instruments have been formed completely by grinding to achieve more constant flexibility along the length, these instruments have significant drawbacks. First, instruments formed completely by grinding are more costly to manufacture. Also, twisted instruments may be formed in a wide variety of cross-sectional shapes, depending on the shape of a initially ground wire blank.

In view of problems in this field, including those problems noted above, it would be desirable to provide an endodontic instrument, such as a file or reamer formed from a twisted blank, in which the size of one diameter or cross-sectional dimension is formed independent of the other to optimize flexibility, strength and other operating characteristics of the instrument. In this manner, instruments of greater taper may be formed with greater flexibility for maneuvering within curved root canals, while also retaining sufficient strength to resist breakage during use.

One improved instrument was disclosed in U.S. patent application Ser. No. 09/288,173, filed Apr. 8, 1999, now pending, assigned to the assignee of the present invention. The disclosure of this prior related application is hereby fully incorporated by reference herein. The instruments disclosed in this prior application utilize a blank in which the grind angles of the edges vary along the length of the blank. This advantageously allows for more flexibility of the instrument, especially in those instruments having a greater taper with increased dimensions at the proximal end of the working length. Nevertheless, there is still a need for improvements in relation to solving the same type of flexibility problems while reducing the difficulty and expense associated with manufacturing the instruments.

SUMMARY OF THE INVENTION

The present invention provides an endodontic instrument, such as a file, reamer or other cutting, shaping or cleaning instrument, comprising an elongate member with optimal flexibility, strength and other operating characteristics. The elongate member includes a longitudinal axis, which is preferably straight when not in use, and a proximal end, a distal end and a working length generally between the proximal and distal ends. The working length is formed with an outer surface comprising a plurality of lengthwise extending surface portions ground therefrom. A plurality of lengthwise extending edges are respectively positioned between adjacent lengthwise extending surface portions. In accordance with one aspect of this invention, the minor diameter is formed independent of the major diameter at one or more locations along the working length. In this manner, the minor diameter may be of any dimension below the major diameter depending on the desired characteristics. As an illustrative example, this may be accomplished by removing at least a portion of one of the lengthwise extending edges of the elongate member to form another surface portion along which the flexibility of the instrument is increased and which defines the minor diameter of the instrument at the location of material removal.

In the preferred embodiments, the principles of this invention are applied to instruments having generally triangular cross sections or generally parallelogram-shaped cross sections. The working length of the instrument is preferably tapered in a direction from the proximal end toward the distal end such that the diameter of the working length decreases in that direction. One or more cutting edges are located along the major diameter of the working length and, in the preferred embodiments, opposite edges lying on the minor diameter are ground off as additional lengthwise extending surface portions that preferably taper less than the remaining lengthwise extending surface portions which define cutting edges therebetween. More preferably, the additional surface portions are formed as zero taper flats.

In accordance with the invention, the instrument will be more flexible than conventional instruments of the same taper. As mentioned above, the invention allows the minor and major diameters of the instrument to be sized independent of one another. This aspect allows the minor diameter or cross sectional dimension to be maintained substantially constant along the working length, while the major diameter or cross sectional dimension includes a taper. Thus, a twisted instrument according to this aspect of the invention will have a more constant flexibility along the working length notwithstanding a significant taper existing along the major diameter. Other embodiments of this general aspect are also possible and include, for example, forming the minor and major diameters with different tapers.

Endodontic instruments of this invention may be formed with many different cross sectional shapes. Typically, the elongate member of the finished instrument will have three or four longitudinally or lengthwise extending helical surface portions and at least one longitudinal, helically-shaped cutting edge. The instrument may be formed from materials having superelastic properties and/or other materials, such as titanium, carbon steel or stainless steel.

A preferred method of making endodontic instruments according to the invention includes removing material from an outer surface of a wire along at least three separate paths extending along the working length to form adjacent first, second and third lengthwise surface portions. The method further includes forming at least three separate edges extending along the working length and each positioned between two adjacent lengthwise surface portions. At least a portion of one of the edges is removed to form at least a fourth lengthwise surface portion and to decrease the diameter of the blank along the fourth lengthwise surface portion. The formed blank is then twisted to form the edges and lengthwise surface portions into helically-shaped edges and surface portions along the working length.

Other features, objects and advantages of the invention will become more readily apparent to those of ordinary skill in the art upon review of the following detailed description of the preferred embodiments, taken in conjunction with the accompanying drawings.

BRIEF DESCRIPTION OF THE DRAWINGS

FIG. 1 is a cross sectional view of a tooth and an endodontic instrument in accordance with the invention shown in use within a root canal;

FIG. 2 is an enlarged elevational view of a portion of the endodontic instrument shown in FIG. 1;

FIG. 3A is an end view of an initial step in a grinding process used to form the endodontic instrument of FIGS. 1 and 2;

FIG. 3B is a view similar to FIG. 3A, but showing a later process step of grinding off at least a portion of one of the edges;

FIG. 3C is a view similar to FIG. 3B, but showing a further part of the same grinding process along the edge;

FIG. 3D is a view similar to FIG. 3C, but showing a grinding process performed on the opposite edge;

FIG. 3E is an end view of the finished ground blank prepared in accordance with FIGS. 3A–3D;

FIG. 4 is a side elevational view of the blank formed in accordance with FIGS. 3A–3D as viewed along the major diameter;

FIG. 5 is a side elevational view similar to FIG. 4, but illustrating the blank along the minor diameter;

DETAILED DESCRIPTION OF THE PREFERRED EMBODIMENTS

Figure 6:
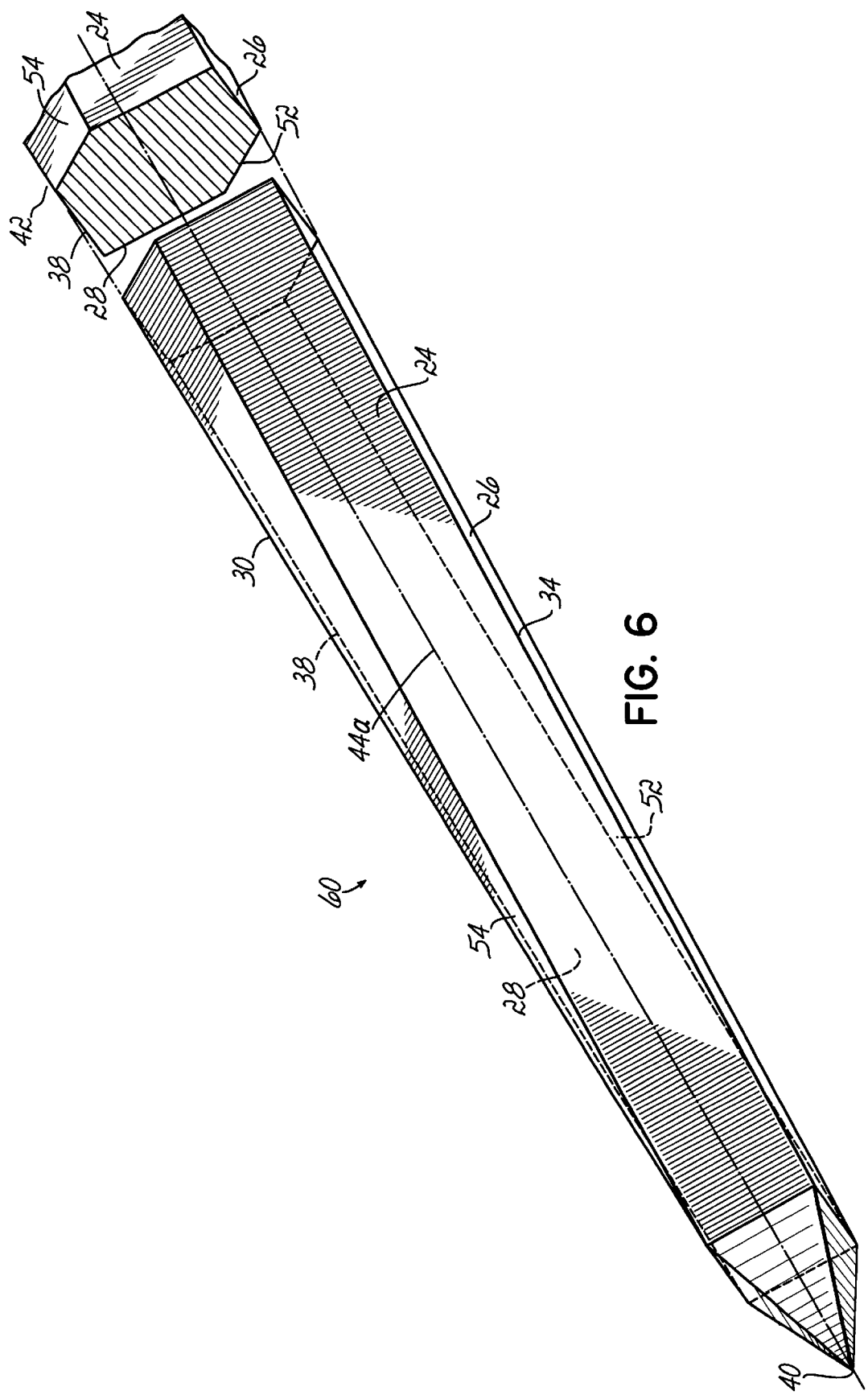
FIG. 6 is a perspective view of the blank ground in accordance with FIGS. 3A–3D.

Referring first to FIG. 1, an endodontic instrument 10 constructed in accordance with a preferred embodiment of the invention is shown being used during a root canal procedure on a tooth 12. Tooth 12 includes root canals 14, 16 and an upper interior portion 18 which has been initially opened using another instrument, such as a drill (not shown). Instrument 10 includes a handle 20 for manual gripping by, for example, an endodontist and a working length 22 having helical flutes, as will be discussed in more detail below. Although these instruments are typically manipulated manually, the invention may be adapted to power-operated instruments as well. In a conventional manner, instrument 10 may be rotated in the direction of arrows "A" and reciprocated in the direction of arrow "B" by the endodontist to clean out and enlarge root canal 16.

As shown in the enlarged view of working length 22 in FIG. 2, respective flutes are formed by twisted surface portions 24, 26, 28, 30. These surface portions 24, 26, 28, 30 are defined between respective edges and surface portions 34, 38, 52, 54. The formation of surface portions 52, 54 will be further described with respect to FIGS. 3A–3E below. As further shown in FIG. 2, and explained in more detail below, a minor diameter or cross-sectional dimension "d" and a major diameter or cross-sectional dimension "D" are evident along the working length 22. Minor diameter "d" preferably remains substantially constant along working length 22, while major diameter "D" becomes progressively larger in a direction extending from distal end 40 to proximal end 42 of working length 22. Due to the substantially constant minor diameter "d" extending along the working length 22, the flexibility of working length 22 is maintained generally constant along working length 22 in the preferred embodiment, however, this is not necessary to realize benefits of the invention. As will also be discussed below, minor diameter "d" may also have a taper along the working length 22 or along a portion or portions thereof so as to increase slightly in diameter from distal end 40 toward proximal end 42. However, the rate of taper is preferably substantially less than the rate of taper of major diameter "D". For example, the rate of taper for minor diameter "d" may be in the range of zero to about 0.06, while the rate of taper for major diameter "D" may be in the range of about 0.02 to about 0.14.

FIGS. 3A–3D illustrate a preferred method of manufacturing instrument 10. In this regard, a cylindrical wire 44 has distal end 40 initially ground to a sharp point. Wire 44 may be formed of any suitable material used for endodontic instruments of this type. As a few examples, such materials include superelastic materials such as NiTi, or other materials such as titanium, carbon steel or stainless steel. A grinding wheel 48 is used to sequentially grind four longitudinally extending surface portions 24, 26, 28, 30 along wire 44. These become the flutes of the final, twisted instrument 10. Specifically, as shown by the end view of wire 44 in FIGS. 3A and 3B, grinding wheel 48 is rotated as wire 44 translates with respect thereto along its center axis 44*a* (FIG. 2). Each longitudinal or lengthwise grinding step forms one of the surface portions 24, 26, 28, 30. To accomplish this, wire 44 is indexed or rotated 90° before starting the grinding operation to form each successive surface portion 24, 26, 28, 30. This simultaneously forms respective edges 32, 34, 36, 38.

In the preferred embodiment, for example, wire 44 may be ground along a working length of about 4 mm to about 23 mm. Wire 44 is translated along grinding wheel 48 at a rate of about 100 in./min depending on the material and the size of wire 44. During each of the grinding operations, as wire 44 translates past grinding wheel 48, grinding wheel 48 is moved away from the center axis 44*a* of wire 44 at a preferred rate of about 0.5 in./min. depending on the wire translation rate mentioned above and the desired taper. This rate may change for the different surface portions. The depth of cut may be about 0.005 inch depending on the instrument size and material and the initial wire diameter is preferably 0.041 inch. At the end of these four grinding steps, a wire blank 44' is formed as shown in FIG. 3B having a conventional square cross-sectional shape. At this point in the process, the major diameter, or largest diameter, of the blank at a given location along the working length 22 is the distance between edges 34 and 38 or the equal distance between edges 32 and 36. The minor diameter, or smallest diameter, is the distance between flats 24 and 28 or the equal distance between flats 26 and 30. In accordance with one aspect of the invention, a new minor diameter "d" will be formed and this new minor diameter "d" will be smaller than the diameter between flats 24, 28 or flats 26, 30 along at least a portion of the working length 22.

In accordance with this embodiment of the invention, and as shown progressively in FIGS. 3B–3D, edges 32 and 36 have at least portions thereof ground off as flats 52, 54. These flats 52, 54 may extend completely along working length 22 or along one or more portions of working length 22. As shown in FIG. 3E, these flats extend along a minor diameter "d" and, in this embodiment, are parallel to each other.

Alternatively, only one flat 52 or 54 may be ground along wire blank 44' and flats 52 and/or 54 may alternatively taper in a direction from proximal end 42 toward distal end 40. Although each of the surface portions 24, 26, 28, 30, 52, 54 are shown as flat or planar surface portions, one or more of the surface portions may have an alternative surface configuration, such as a concave configuration, as long as the surface portion is generally flattened as opposed to being a sharp edge. In the above-described manner, a fully ground blank 60 as shown in FIGS. 3E, 4, 5 and 6, is constructed and ready to be physically twisted by any suitable method known to those of skill in the art to form a final tissue removing instrument 10 as shown in FIG. 2. One suitable twisting method is disclosed in U.S. Pat. No. 6,149,501, assigned to the assignee of the present invention and the disclosure of which is hereby fully incorporated by reference. As further shown in FIGS. 4, 5 and 6, ground blank 60 will have a minor diameter "d", as shown in FIG. 4, which may be substantially constant or slightly tapered along working length 22. A major diameter "D", as shown in FIG. 5, tapers more significantly as shown by dimensions T1, T2, T3 which decrease in a direction from the proximal end (not shown) toward the distal end 40. As further shown in FIG. 6, each surface portion 24, 26, 28, 30 gradually widens in a direction from distal end 40 toward proximal end 42. The cross section of ground blank 60, in this embodiment, transforms from a relatively square cross section proximate distal end 40 to a six-sided cross section at proximal end 42.

Figure 7:
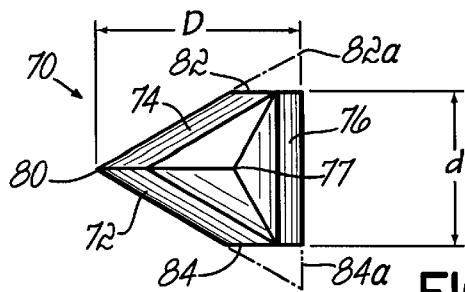
FIG. 7 is an end view of an alternative wire blank constructed in accordance with the invention.
Figure 8:
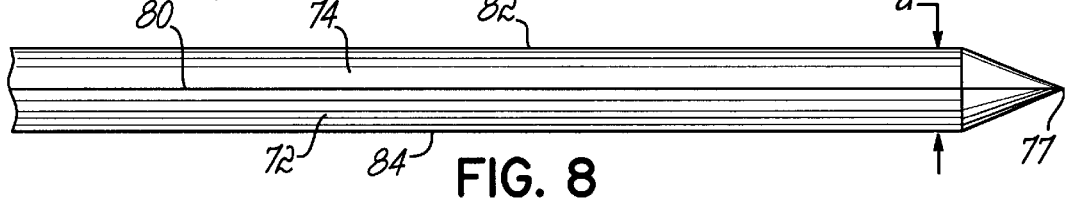
FIG. 8 is a side elevational view illustrating the wire blank of FIG. 7 along the minor diameter.
Figure 9:
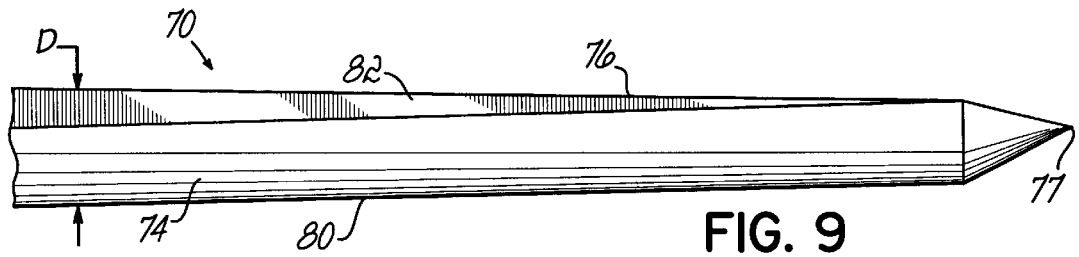
FIG. 9 is a side elevational view similar to FIG. 8, but illustrating the wire blank along the major diameter.
Figure 11:
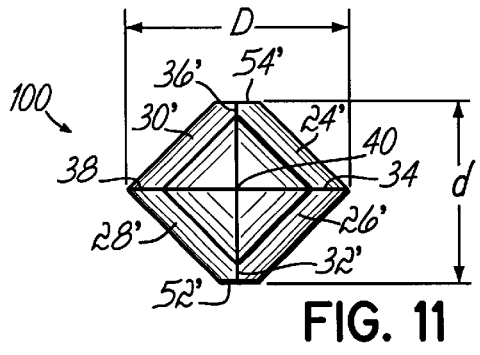
FIG. 11 is an end view of another alternative embodiment of the invention.
Figure 12:
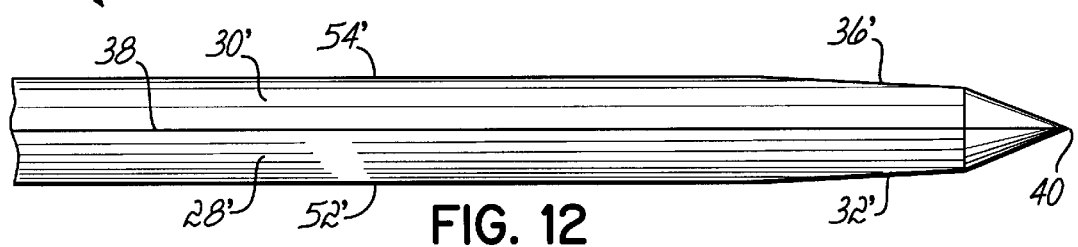
FIG. 12 is a side elevational view of the wire blank shown in FIG. 11 and illustrated along the major diameter.

FIGS. 7–10 illustrate an alternative embodiment of the invention having a generally triangular-shaped cross section as will be appreciated from the end view of the ground blank 70 illustrated in FIG. 7. This embodiment is ground in a similar manner to the process described in connection with FIGS. 3A–3D, except that a wire is initially formed into a triangular-shape, in cross section, by indexing the wire 120° after each lengthwise grinding operation to form respective lengthwise extending surface portions 72, 74, 76. Surface portions 72, 74, 76 ultimately become the helical flutes of the final twisted instrument (not shown). As with the first embodiment, the distal end 77 is again ground to a sharp point. A lengthwise cutting edge 80 is formed between surface portions 72, 74. The two remaining opposite edges 82*a*, 84*a* extending along the ground blank 70 are at least partially ground into parallel flat surface portions 82, 84 as shown best in FIG. 7. This forms a new smaller minor diameter "d" and increases the flexibility along the length of the wire blank 70 and the resulting instrument. In this embodiment, the flexibility will also be constant along the working length of the finished instrument since the minor diameter "d" remains constant along the working length. As with the first embodiment, various changes may be made from this preferred design including, for example, tapering the surface portions 82, 84, using only one surface portion 82 or 84, and/or changing the surface configuration of the one or both of surface portions 82, 84. Upon forming the fully ground wire blank 70, the wire blank 70 is physically twisted such that the surface portions 72, 74, 76, 82, 84 and cutting edge 80 take on a helical shape, as in the first embodiment, but only having one cutting edge 80 and three helical flutes 72, 74, 76.

Figure 13:
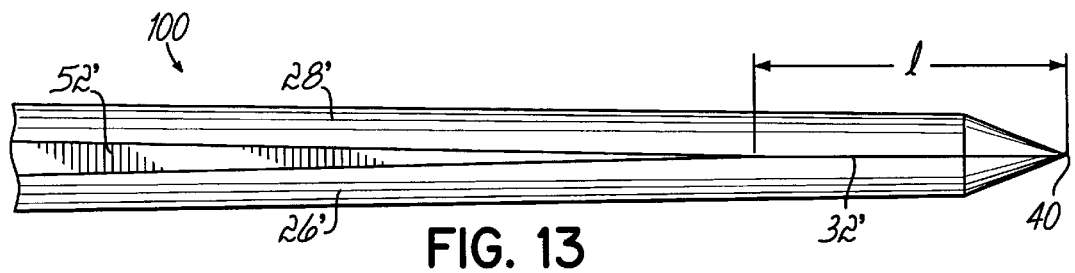
FIG. 13 is a side elevational view similar to FIG. 12, but illustrating the wire blank along the minor diameter.
Figure 10:
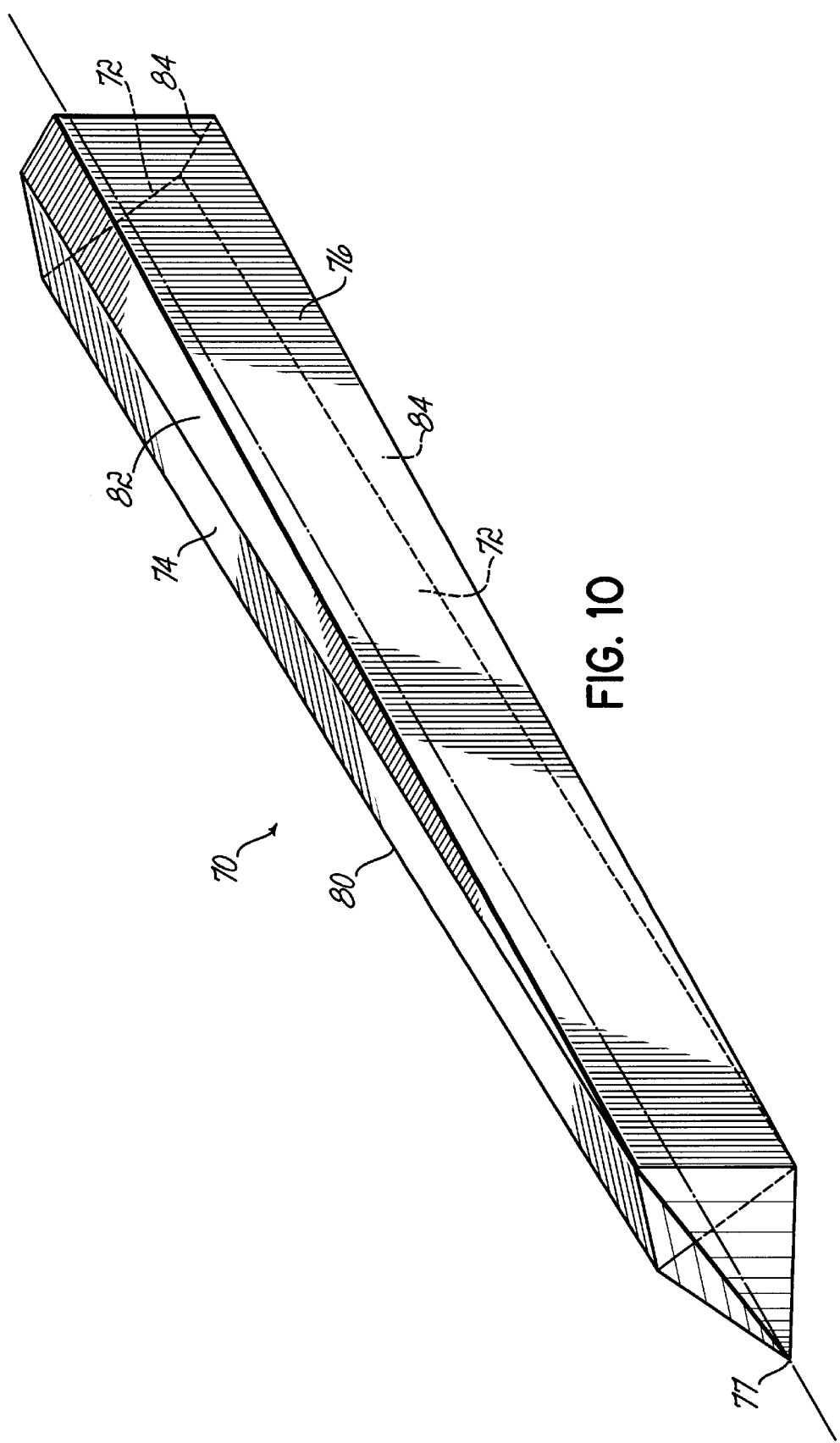
FIG. 10 is a perspective view of the wire blank illustrated in FIGS. 7–9.
Figure 14:
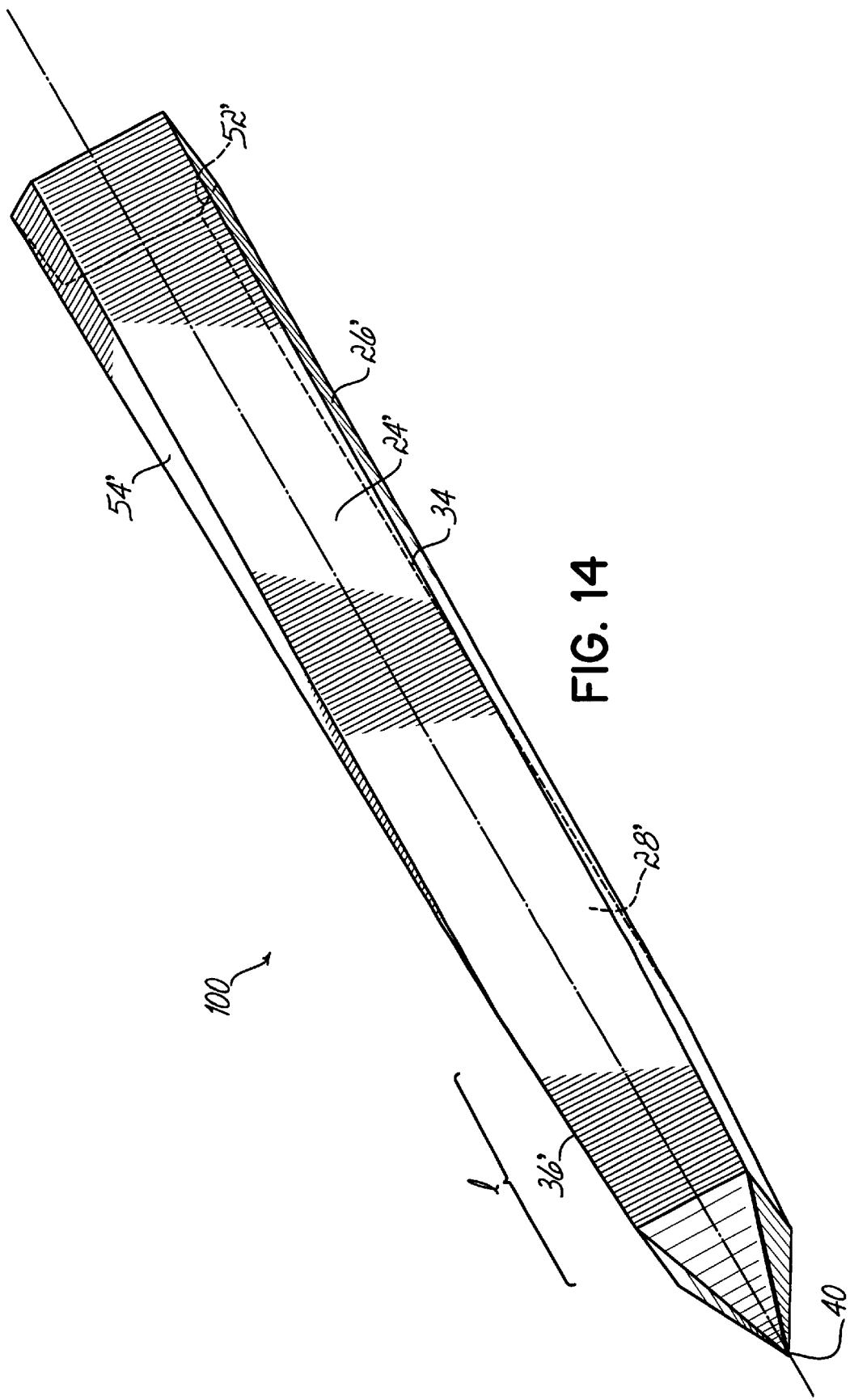
FIG. 14 is a perspective view illustrating the wire blank of FIGS. 11–13.

FIGS. 11–14 illustrate another alternative embodiment of a fully ground wire blank 100. In this embodiment, like reference numerals to the first embodiment refer to like elements, while numerals with prime marks (') refer to somewhat modified elements as will be apparent from the drawings. Further repeated discussion of like or similar elements is not necessary. This wire blank 100 is similar to the wire blank 60 illustrated in the first embodiment, except that the grinding operation along edges 32, 36 starts at a length e from the distal end 40 as shown in FIG. 13. Therefore, surface portions 52', 54' are formed and will increase the flexibility of the resulting instrument more at the proximal end of the working length while not increasing the flexibility of the working length toward the distal end 40. In many cases, the distal end portion may already have sufficient flexibility and, therefore, may not need the additional grinding operation performed along the minor diameter as described in connection with this invention. In this embodiment, as well as the previous embodiments, the angle of grind of any of the surface portions may change along the working length. Ground blank 100 is physically twisted to form a final instrument as in the first and second embodiments.

While the present invention has been illustrated by a description of the preferred embodiments and while these embodiments have been described in some detail, it is not the intention of the Applicant to restrict or in any way limit the scope of the appended claims to such detail. Additional advantages and modifications will readily appear to those skilled in the art. This has been a description of the present invention, along with the preferred methods of practicing the present invention as currently known. However, the invention itself should only be defined by the appended claims, wherein

I claim:

1. A method of making an endodontic instrument from a wire having an outer surface, a longitudinal axis, a proximal end and a distal end, the method comprising:
   removing material from the outer surface of the wire along at least three separate paths extending along the longitudinal axis to form a working length with adjacent first, second and third lengthwise surface portions,
   forming at least three separate edges extending along the working length and each positioned between two adjacent lengthwise surface portions thereby forming a ground wire blank having a major diameter and a smaller, first minor diameter,
   removing at least a portion of one of the edges to form at least a fourth lengthwise surface portion lying alone a second minor diameter of the blank smaller than the first minor diameter, the width of the one edge being less than the respective widths of the first, second and third surface portions at the same location along the working length, and
   twisting at least one of the proximal and distal ends with respect to the other and about the longitudinal axis to form said edges and lengthwise surface portions into helically shaped edges and surface portions along the working length.

2. A method of making an endodontic instrument from a wire having an outer surface, a longitudinal axis, a proximal end and a distal end, the method comprising:
   removing material from the outer surface of the wire along at least three separate paths extending along the longitudinal axis to form a working length with adjacent first, second and third lengthwise surface portions,
   forming at least three separate edges extending along the working length and each positioned between two adjacent lengthwise surface portions thereby forming a ground wire blank having a major diameter and a smaller, first minor diameter,
   removing at least a portion of two of the edges to form at least fourth and fifth lengthwise surface portions on generally opposite sides of the longitudinal axis for defining a second minor diameter between the fourth and fifth lengthwise surface portions smaller than the first minor diameter, the fourth and fifth lengthwise surface portions being parallel to each other, and
   twisting at least one of the proximal and distal ends with respect to the other and about the longitudinal axis to form said edges and lengthwise surface portions into helically shared edges and surface portions alone the working length.

3. The method of claim 2, wherein the second minor diameter is is formed by the fourth and fifth lengthwise surface portions.

4. The method of claim 2, wherein the twisting step is performed on the wire blank such that one of the at least three separate edges defines a cutting edge.

5. The method of claim 2, further comprising:
   prior to twisting the wire blank, removing material from the outer surface of the wire blank to form a sixth lengthwise surface portion,
   wherein the twisting step is performed on the wire blank such that two of the at least three separate edges define two cutting edges.

6. An endodontic instrument for removing dental tissue, the instrument comprising:
   an elongate member including a longitudinal axis, a proximal end, a distal end, a major diameter and a smaller, minor diameter and a working length with an outer surface generally located between the proximal and distal ends,
   first, second and third lengthwise extending surface portions each forming part of the outer surface and tapering along the longitudinal axis in a direction from the proximal end toward the distal end, said first, second and third lengthwise extending surface portions forming a generally triangular cross sectional shape,
   a lengthwise extending cutting edge lying along the major diameter and formed at a junction between said first and second lengthwise extending surface portions, and
   a fourth lengthwise extending surface portion lying on the minor diameter and formed at a junction between said first and third lengthwise extending surface portions, each of said first, second, third and fourth lengthwise extending surface portions lying in separate planes.

7. The endodontic instrument of claim 6, wherein said first, second, third and fourth lengthwise extending surface portions are flats.

8. An endodontic instrument for removing dental tissue, the instrument comprising:
   an elongate member including a longitudinal axis, a proximal end, a distal end, a major diameter and a smaller, minor diameter and a working length with an outer surface generally located between the proximal and distal ends,
   first, second and third lengthwise extending surface portions each forming part of the outer surface and tapering along the longitudinal axis in a direction from the proximal end toward the distal end, said first, second and third lengthwise extending surface portions forming a generally triangular cross sectional shape,
   a lengthwise extending cutting edge lying along the major diameter and formed at a junction between said first and second lengthwise extending surface portions, and
   fourth and fifth lengthwise extending surface portions lying on the minor diameter, said fourth lengthwise extending surface portion formed at a junction between said first and third lengthwise extending surface portions and said fifth lengthwise extending surface portion formed at a junction between said second and third lengthwise extending surface portions, said fourth and fifth lengthwise extending surface portions being parallel to each other.

9. An endodontic instrument for removing dental tissue, the instrument comprising:
   an elongate member including a longitudinal axis, a proximal end, a distal end, a major diameter and a smaller, minor diameter and a working length with an outer surface generally located between the proximal and distal ends,
   first, second, third and fourth lengthwise extending surface portions each forming part of the outer surface and tapering along the longitudinal axis in a direction from the proximal end toward the distal end, said first, second, third and fourth lengthwise extending surface portions forming a generally parallelogram-shaped cross section, a first lengthwise extending cutting edge lying on the major diameter and formed at a junction between said first and second lengthwise extending surface portions, a second lengthwise extending cutting edge lying on the major diameter and formed at a junction between said third and fourth lengthwise extending surface portions, and a fifth lengthwise extending surface portion having a taper less than the respective tapers of the first, second, third and fourth lengthwise extending surface portions said fifth lengthwise extending surface portion formed at a junction between said second and third lengthwise extending surface portions.

10. The endodontic instrument of claim 9 further comprising:

a sixth lengthwise extending surface portion lying on the minor diameter and formed at a junction between said first and fourth lengthwise extending surface portions.

11. The endodontic instrument of claim 10, wherein said fifth and sixth lengthwise extending surface portions have zero tapers and are parallel to each other.

12. The endodontic instrument of claim 9, wherein said first, second, third, fourth and fifth lengthwise extending surface portions are flats.

13. An endodontic instrument for removing dental tissue, the instrument comprising:

an elongate member including a longitudinal axis, a proximal end, a distal end, a major diameter and a smaller, minor diameter and a working length with an outer surface generally located between the proximal and distal ends, and a plurality of lengthwise extending surface portions each forming part of the outer surface and tapering in a direction from the proximal end to the distal end, and a plurality of lengthwise extending edges positioned between adjacent lengthwise extending surface portions, at least one of said edges being a cutting edge extending along the working length, at least one additional lengthwise extending surface portion forming part of the outer surface and tapering less than each of said plurality of lengthwise extending surface portions.

14. The endodontic instrument of claim 13 wherein the working length of said instrument is generally triangular shaped in transverse cross section and said cutting edge lies along said major diameter.

15. The endodontic instrument of claim 13, further comprising at least two of said additional lengthwise extending surface portions.

16. The endodontic instrument of claim 15, wherein said two additional lengthwise extending surface portions have zero tapers and are parallel to each other.

17. The endodontic instrument of claim 13, wherein the working length of said instrument is generally parallelogram shaped in transverse cross section and further comprising an additional cutting edge between two of said plurality of lengthwise extending surface portions.

18. The endodontic instrument of claim 17, wherein said cutting edges are positioned on opposite sides of the longitudinal axis along said major diameter.

* * * * *

UNITED STATES PATENT AND TRADEMARK OFFICE
CERTIFICATE OF CORRECTION

PATENT NO.    : 6,712,611 B2
DATED         : March 30, 2004
INVENTOR(S)   : Gary T. Garman It is certified that error appears in the above-identified patent and that said Letters Patent is hereby corrected as shown below:

Column 1,
Line 23, reads "...protective cement. The endodontists may sometimes apply a..." and should read -- ... protective cement. The endodontist may sometimes apply a ... --.

Column 5,
Lines 50-51, reads "...other. (new paragraph) Alternatively, only one flat 52 or 54 may be ground along..." and should read -- ...other. Alternatively, only one flat 52 or 54 may be ground along... --.
Lines 66-67, reads "...hereby fully incorporated by reference. As further shown in FIGS. 4, 5 and 6, ground blank 60 ..." and should read -- ...hereby fully incorporated by reference. (new paragraph) As further shown in FIGS. 4, 5 and 6, ground blank 60 ... --.

Column 6,
Line 52, reads "...length e from the distal end 40 as shown in Fig. 13." and should read -- ...length 1 from the distal end 40 as shown in FIG. 13. --.

Column 7,
Line 23, reads "...least a fourth lengthwise surface portion lying alone a..." and should read -- ...least a fourth lengthwise surface portion lying along a ... --.
Line 56, reads "...helically shared edges and surface portions alone the..." and should read -- ...helically shaped edges and surface portions along the... --.
Line 59, reads "...diameter is is formed by the fourth and fifth lengthwise..." and should read -- ...diameter is formed by the fourth and fifth lengthwise ... --

UNITED STATES PATENT AND TRADEMARK OFFICE
CERTIFICATE OF CORRECTION

PATENT NO. : 6,712,611 B2
DATED : March 30, 2004
INVENTOR(S) : Gary T. Garman

It is certified that error appears in the above-identified patent and that said Letters Patent is hereby corrected as shown below:

Column 9,
Line 10, reads "...and fourth lengthwise extending surface portions said..." and should read -- ...and fourth lengthwise extending surface portions, said... --.

Signed and Sealed this

Third Day of May, 2005

JON W. DUDAS
*Director of the United States Patent and Trademark Office*